United States Patent [19]

Mercati

[11] Patent Number: 6,039,953
[45] Date of Patent: Mar. 21, 2000

[54] HIGHLY CONCENTRATED MINERALISED NATURAL COMPLEX FOR THE INTEGRATION OF MINERAL OLIGOELEMENTS AND METHOD FOR ITS PRODUCTION

[75] Inventor: Valentino Mercati, Città di Castello, Italy

[73] Assignee: Aboca di Mercati Valentino & C. Societa Semplice, Sansepolcro Arezzo, Italy

[21] Appl. No.: 09/195,249

[22] Filed: Nov. 18, 1998

[30] Foreign Application Priority Data

Dec. 23, 1997 [EP] European Pat. Off. .............. 97830706

[51] Int. Cl.[7] .......................... A61K 35/78; A61K 33/24
[52] U.S. Cl. ...................... 424/195.1; 424/464; 424/617; 424/646; 424/678; 424/681; 424/687; 424/692; 424/693; 426/615; 426/648
[58] Field of Search ................................ 424/195.1, 464, 424/617, 646, 678, 681, 687, 692, 693, 520; 426/615, 648

[56] References Cited

U.S. PATENT DOCUMENTS 4,915,946  4/1990  Kang ..................................... 424/195.1
5,405,613  4/1995  Rowland ................................ 424/439

FOREIGN PATENT DOCUMENTS 9003291  1/1992  Brazil .
6097231  8/1981  Japan .
8073213  3/1996  Japan .

OTHER PUBLICATIONS

AN 92–065215, Class D16, BR 9003291, Jan. 28, 1992–Abstract.
AN 96–206316, Class D13, JP 08 073 213, Mar. 19, 1996–Abstract.

*Primary Examiner*—Leon B. Lankford, Jr.
*Assistant Examiner*—Christopher R. Tate
*Attorney, Agent, or Firm*—Dennison, Meserole, Scheiner & Schultz

[57] ABSTRACT

The invention concerns a highly concentrated mineralised natural complex, characterised by at least one main mineral element quantified with nutritional and/or dietetic integrator properties and by other mineral elements obtained in the complex from the mineralization of vegetal and/or animal products. Moreover, it concerns the method for its production consisting in using vegetal and/or animal organic substances, having a high content of oligominerals, in carrying out their fragmentation, their mixing and the mineralization until the inorganic part is completely separated from the organic part, and then in transforming the aforesaid inorganic part in forms of easy commercialization.

7 Claims, 1 Drawing Sheet

Figure
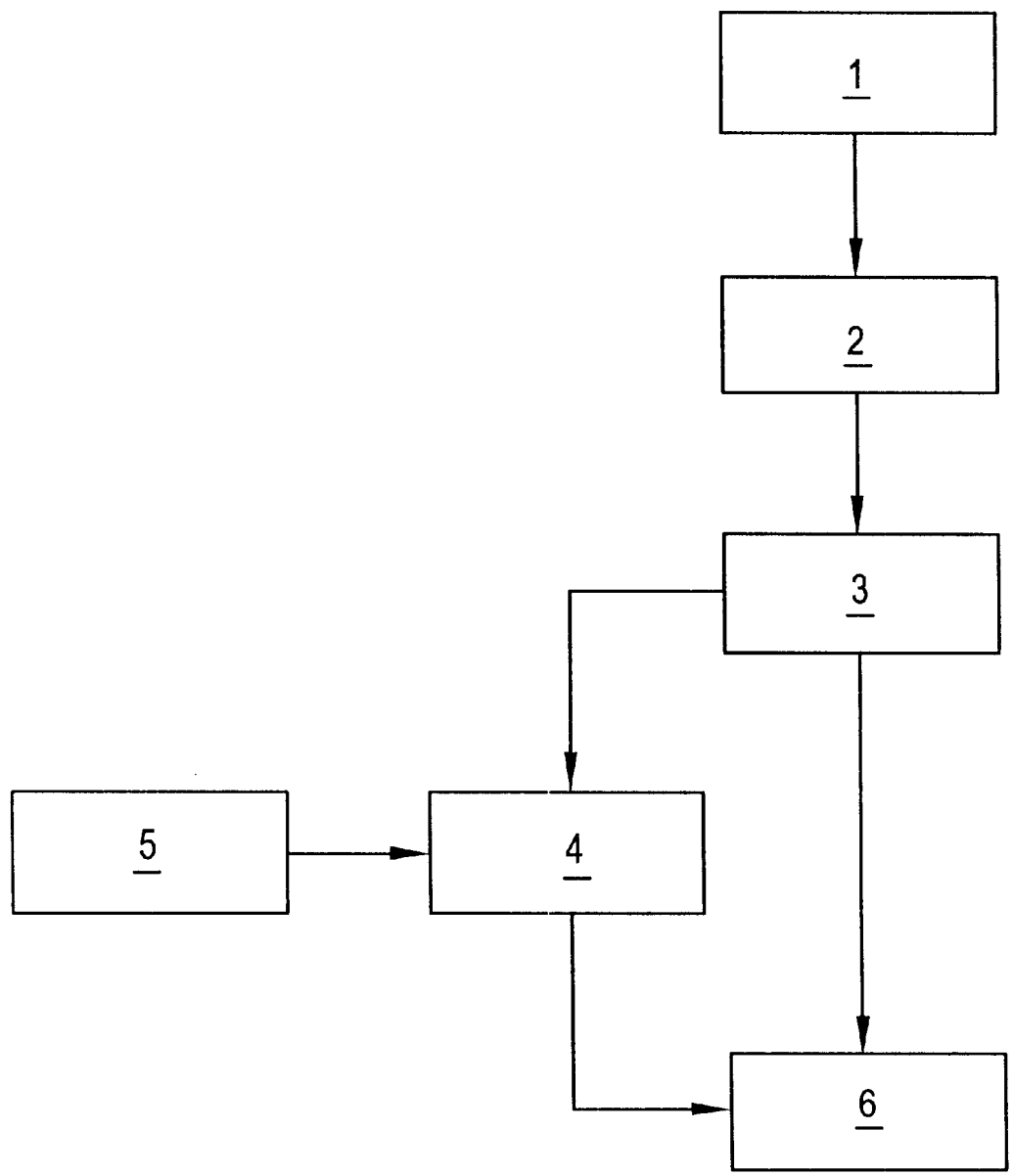

HIGHLY CONCENTRATED MINERALISED NATURAL COMPLEX FOR THE INTEGRATION OF MINERAL OLIGOELEMENTS AND METHOD FOR ITS PRODUCTION

BACKGROUND OF THE INVENTION

1. Field of the Invention

The invention concerns a highly concentrated mineralised natural complex and the method for its production, with respect to the integration of mineral oligoelements in pharmaceutical, cosmetic and herbal field, for human and animal usage, and for the care of the flora in general.

2. Description of Related Art

Currently, elements obtained by the purification of inorganic material, or, for example, through operations of synthesis, hemi-synthesis, chelation, complexation are being used as integrators of minerals oligoelements.

The so obtained inorganic formulations present considerable problems of absorption and side effects. The ingested substances are thereby absorbed in a very little amount, consequently inducing the user to ingest considerable quantities, so that the absorbed ones can quantitatively satisfy the individual need.

Another disadvantage of the products obtained with the known technique is the one due to the undesired side effects, for example, after the ingestion of substances used for integrating iron gastric disturbances may occur.

On the other hand, it is known that some organic substances, such as some vegetable and/or animal products, contain oligominerals that are effective for man's health and simultaneously do not have negative side effects. However, those elements useful for man's health are contained in the above mentioned organic substances in very small percentages, hence they have poor therapeutic qualities.

SUMMARY OF THE INVENTION

The aim of the present invention is on the one hand to produce mineralised natural complexes of one or more mineral elements at a high concentration, which together predispose the human organism to their high absorption without producing negative side effects, on the other hand, the aim is to determine a process through which the mentioned complexes are realised.

The process, related to this invention, which allows to reach such results, consists in resorting to natural substances, like vegetable and/or animal products, then, usually, in the carrying out of their mixing in definite proportions, therefore in their treatment until the inorganic part is separated from the organic one, and finally, in the transformation of the produced minerals blend into an easily administrated product, like capsules and tablets. For the consumer their intake is the equivalent to the intake of a quantity of minerals comparable in a qualitative and quantitative way to the ones that would be taken, in favourable cases, with the ingestion of an initial high quantity of vegetable or animal material. Moreover, the elaboration of organic natural products, among those containing an oligo-mineral mixture as close as possible to the wanted optimum, allows to obtain a mineral formulation that has a high biological affinity for man, with a greater bio-availability and compared with those that are nowadays on the market less harmful side effects. These formulation which for the complexity of the elements contained even in traces, cannot absolutely be chemically reconstructed. The invention through which such results have been reached, is realised on the one hand with natural mineralised complexes with a high concentration of one or more main elements of vegetable and/or animal origin and a plurality of other elements equally useful to the human organism, and on the other hand with a process for their production realised through the mixing, in definite proportions, of the vegetal or animal products to be mineralised, and also with their mineralization through the elimination of the organic portion.

Such process is, therefore, characterised by the treatment of natural organic products in order to obtain a mineralised complex containing all the mineral substances originally contained in the raw material treated first in form of oxides and other salts. Such mineralised complexes will be titrated in each element by considering those that are contained in a larger quantity, for example calcium, iron, zinc, potassium, copper, magnesium and manganese, and the aforesaid mineralised complexes will be finally checked to ascertain the absence of elements recognised as toxic, such as lead, cadmium and mercury.

The mineralised natural complexes so produced permit to reach advantageous results, as described here below, unlike the use of single mineral elements obtained with methods known nowadays.

In particular, they allow the organism to be integrated not only with the single primary elements, prevailing in the mineralised complex, but also with an innumerable series of other useful minerals that the mineralised complex contains in a composition which is formulated in nature. For instance, instead of assuming only "Gluconate Iron" as with the existing technique, the mineralised complex is taken as obtained from a mixture of vegetal products such as *Capsella bursa pastoris*, of which the upper part is used, Cynara of which the leaves are used, *Salvia offinalis*, of which the leaves are used. Such complex allows to intake iron in form of oxide and salts together with many other oligoelements, such as calcium, zinc, magnesium, potassium, sodium, copper and manganese, besides other ones in tiny traces, which aid the assimilation of iron without creating harmful side effects.

The elaboration of natural organic products allows, that is to say, to produce a mineralised complex from which the human organism perfectly absorbs most of the various oligomineral elements contained in the same complex. The natural formula, possessing precise qualitative and quantitative relations of the single elements—probably due to biological affinity—determines a much greater absorption than the one obtained by ingesting the single elements presently used. Both the ratios between the single elements and the association between the single substances can be the cause of the considerable absorption of these last ones by the organism. In fact, many of the substances present in minimum doses, even if untraceable, act as catalysts, therefore helping the absorption of the primary element needed for the desired integration.

Another advantage is due to the minor side effects resulting from the nature of the formulation more compatible with man.

BRIEF DESCRIPTION OF THE DRAWING

More characteristics of the invention will be evident from the following detailed description with reference to the process illustrated on the block diagram, provided only as example, in the enclosed drawing, which shows in schematic form a flow diagram of the apparatus elements associated with performing the invention, and the steps of the invention.

DESCRIPTION OF THE PREFERRED EMBODIMENTS

In the process exemplified in the drawing figure:

1 indicates the tank containing the mixture of vegetable and/or animal natural products, each one in a clean and fragmented state, containing one or more primary mineral elements in addition to those in smaller quantities, combined with organic substances to be eliminated;

2 indicates the heated cell, normally at a temperature included between 200° and 900° C., in which the mixture coming from container 1 is mineralised, therefore the organic portion is normally separated in vapours and fumes.

The mineralised complex in container 3 is a mineral complex characterised by a qualitative and quantitative composition of the chosen primary mineral elements, each one combined with a plurality of mineral elements already present, sometimes in minimum measures, on the vegetal and/or animal products from which they are originally produced and contained. The product coming out from group 3 is in one case conveyed directly to chamber 6, and in the other case conveyed to mixer 4 in which it is mixed with other active principles coming from container 5 in order to originate in chamber 6 the mixture that is to be transformed into capsules or tablets, then to be packed and after distributed on the market.

In the general formulation the production process of a mineral complex first foresees the quantitative determination of the metals that one wishes to integrate, hence a selection of the vegetal and/or animal raw materials that present a particularly high content of the above-mentioned metals. After having accomplished the choice of the organic raw materials to be used, the process through which the wanted mineral complex is obtained, can be described in a detailed way as follows:

The chosen raw materials are analysed to make sure that the element is to be integrated is constant in them.

The selected raw materials are dried, then individually cut and sieved until obtaining a uniform granulometry that is adapted for being mineralised.

The previously processed raw materials as described above, are eventually mixed between them in the right proportion in order to obtain in the final complex the content of principal elements as wanted in the ratio. The aforesaid mixture is distributed on trays of stainless steel until reaching a layer of 5 cm. for each tray. The trays are stacked in a muffle one on top of the others, with some space between them for combustion fumes to escape.

The normally methane operating muffle is programmed in such a way to reach within it a temperature of approximately 200–400° C. for 1–3 hours, then it is raised to a temperature of about 500–900° C. for 3–5 more hours, or anyway until the complete removal of the organic portion from the mixture of drugs introduced. The first period of time, at a temperature of 200–400° C., is essential in order to obtain a perfect light coloured mineralised product, without any carbonised organic products.

The mineralised product obtained from the muffle is subjected to a quantitative analysis for being titrated, at least in its main elements, and to a control in order to verify the absence of elements recognised as toxic. It can be conveyed in the packaging division, or first mixed with additional chosen active principles, and hence sent to the packaging.

However, the invention is illustrated here as follows with reference to two applications for the production of different highly concentrated mineralised natural complexes.

EXAMPLE 1

A Mineral Complex Particularly Rich in Iron

Drugs used:

*Capsella bursa pastoris*, of which the upper part is used;

*Cynara scolymus*, of which the leaves are used;

*Salvia officinalis*, of which the leaves are used

The proportion for the mixing has been chosen according to the content of iron in the single drugs above-indicated, in particular:

*Capsella bursa pastoris*: 20%

*Cynara scolymus*: 70%

*Salvia officinalis*: 10%

The selected vegetal drugs have been cut until reaching a uniform granulometry that is adequate to be mineralised. The optimal granulomethy is the following:

*Capsella bursa pastoris*: 1.5–2.0 mm.

*Cynara scolymus*: 1.5–2.0 mm.

*Salvia officinalis*: 1.5–2.0 mm.

The aforesaid fragmented mixture has been distributed on the stainless steel trays until reaching a layer of about 5 cm. of drug for each tray. The trays are stacked one on top of the other, with some space between them for the combustion fumes to escape. The methane operating muffle is programmed to reach within it a temperature of approximately 300° C. for a time of 2 hours at first, then it is raised and kept at a temperature of approximately 700° C. for 4 more hours. The first step at 300° C. is essential in order to obtain a perfect white coloured final product completely inorganic. The mineralised product is encapsulated in gelatine capsules with a final weight of about 500 mg. In this process the obtained mineralised complex contains all the mineral substances originally contained in the raw materials in form of oxides and other salts. The composition of the mineralised complex is the following:

| Element | Concentration in the complex in mg/g |
| --- | --- |
| Iron | 7.73 |
| Calcium | 109.8 |
| Zinc | 0.19 |
| Magnesium | 21.75 |
| Potassium | 85.0 |
| Sodium | 9.3 |
| Copper | 0.03 |
| Manganese | 0.49 |

Due to the high concentration of iron and the relatively high specific weight of the mineralised complex, only four capsules a day are sufficient to obtain a good daily integration of such element (the daily recommended ration of iron is 14 mg. according to the Italian Law). As a matter of fact, the solubility, and therefore the bio-availability with a pH: 1, is extremely high: in fact 2 g. of product are 93.05% soluble in one litre of hydrochloric acid with a pH: 1 at 37° C. (liquid simulating gastric juice).

EXAMPLE 2

A Mineral Complex Particularly Rich in Calcium

Drugs used:

*Paretaria officinalis*, of which the upper part is used;

*Urtica dioica*, of which the leaves are used;

*Eucalyptus globulus*, of which the leaves are used;
*Ginkgo biloba*, of which the leaves are used.

The proportions for the mixing have been chosen according to the calcium content in the single above-mentioned drugs, in particular:

*Paretaria officinalis*: 10%
*Uttica dioica*: 50%
*Eucalyptus globulus*: 30%
*Ginkgo biloba*: 10%

The selected vegetable drugs have been cut until reaching a uniform granulometiy, adequate for being mineralised. The optimal granulometry for each drug is the following:

*Paretaria officinalis*: 1.5–2.0 mm.
*Urtica dioica*: 1.5–2.0 mm.
*Eucalyptus globulus*: 1.5–2.0 mm.
*Ginkgo biloba*: 1.5–2.0 mm.

After having mixed the drugs, separately chopped up by following the above-mentioned granulometry, the mixture is distributed on steel trays until reaching a layer of 5 cm. of drug for each tray. The trays are stacked one on top of each other, with some space between them for the combustion fumes to escape.

The muffle, normally heated with methane, is programmed in such a way to reach within it a temperature of approximately 300° C. for 2 hours, then it is raised and kept at a temperature of about 700° C. for 4 more hours. The first step at 300° C. is essential in order to obtain a perfect white coloured final product and completely inorganic. The mineralised product is encapsulated in gelatine capsules with a final weight of about 500 mg. In this process the obtained mineralised complex contains all the mineral substances originally contained in the raw materials in form of oxides and other salts. The composition of the obtained mineralised complex is the following:

| Element | Concentration in the complex in mg/g. |
|---|---|
| Iron | 1.9 |
| Calcium | 299.5 |
| Zinc | 0.46 |
| Magnesium | 33.74 |
| Potassium | 94.6 |
| Sodium | 8.5 |
| Copper | 2.5 |
| Manganese | 4.08 |

Due to the high concentration of calcium and the relatively high specific weight of the mineralised complex, only five capsules per day are sufficient to obtain a good daily integration of calcium (in Italy the recommended daily ration of calcium is of 800 mg.). In fact, the solubility, and so the bio-availability with a pH: 1, is extremely high: 2 g. of product are 77.15% soluble in a little of hydrochloric acid with a pH: 1 at 37° C. (liquid simulating gastric juice). The process is repeated for any other individually chosen vegetal and/or animal product, or in combination with other organic products characterised by a high content of metal or metals, through which the integration of mineral oligoelements in humans, animals or plants is intended to be operated.

What is claimed is:

1. A method for production of an inorganic mineral concentrate product, comprising obtaining a plurality of organic starting materials of vegetable origin having a mineral content, determining the mineral content of the plurality of organic starting materials, mixing said starting materials together to obtain a mixture having a mineral content corresponding to the product, and removing organic material from the mixture by heating the mixture at a temperature of 200° to 400° C. for 1 to 3 hours to obtain a light colored inorganic product, followed by heating the mixture to a temperature of 500° to 900° C. for 3 to 5 hours, to obtain the inorganic mineral concentrate product.

2. The method of claim 1, additionally comprising individually cutting and sieving each of the starting materials prior to said mixing to obtain a uniform granulometry adapted for mineralization.

3. The method of claim 1, additionally comprising quantitative analysis of the product.

4. The method of claim 1, additionally comprising mixing the product with at least one additional material and packaging the mixture with the at least one additional material in a dosage form.

5. The method of claim 1, wherein the product is rich in iron, and the organic starting materials comprise, by weight, 20% upper part *Capsella bursa pastoris*, 70% leaves of *Cynara scolymus* and 10% leaves of *Salvia officinalis*, and the organic material is removed by heating in a methane heated muffle at an initial temperature of 300° C. for two hours, followed a final temperature of 700° C. for four hours, to obtain a product having an iron content of about 7.73 mg/g.

6. The method of claim 1, wherein the product is rich in calcium, and the starting materials comprise, by weight, 10% upper part *Paretaria officinalis*, 50% leaves of *Urtica dioica*, 30% leaves of *Eucalyptus globulus* and 10% leaves of *Gingko biloba*, and the organic material is removed by heating in a methane heated muffle at a temperature of 300° C. for two hours, followed by 700° C. for four hours, to obtain a product having a calcium content of about 299.5 mg/g.

7. The method of claim 1, wherein the product is packaged in gelatin capsules.

* * * * *